(12) United States Patent
Prockop et al.

(10) Patent No.: US 7,018,803 B2
(45) Date of Patent: Mar. 28, 2006

(54) INHIBITORS OF COLLAGEN ASSEMBLY

(75) Inventors: Darwin J. Prockop, Philadelphia, PA (US); Andrzej Fertala, Voorhees, NJ (US)

(73) Assignee: Drexel University College of Medicine, Philadelphia, PA (US)

( * ) Notice: Subject to any disclaimer, the term of this patent is extended or adjusted under 35 U.S.C. 154(b) by 442 days.

(21) Appl. No.: 10/279,991

(22) Filed: Oct. 24, 2002

(65) Prior Publication Data

US 2003/0087315 A1 May 8, 2003

Related U.S. Application Data

(60) Division of application No. 09/517,866, filed on Mar. 3, 2000, now Pat. No. 6,472,504, which is a continuation of application No. PCT/US98/18838, filed on Sep. 10, 1998.

(60) Provisional application No. 60/058,353, filed on Sep. 10, 1997.

(51) Int. Cl.
*G01N 33/53* (2006.01)

(52) U.S. Cl. ..................................... 435/7.1

(58) Field of Classification Search ................. 435/7.1
See application file for complete search history.

(56) References Cited

U.S. PATENT DOCUMENTS 5,334,702 A 8/1994 Greene et al.

OTHER PUBLICATIONS

Prockop et al. J. Biol. Chem 273(25): 15598-15604.*
Bhatnagar et al., 1997, J. Biomolec. Struct. Dynamics 14:547-560.
Brodsky and Eikenberry, 1982, Methods Enzymol. 82:127-173.
Brown et al., 1977, Biochem. Biophys. Res. Commun. 74:1102-1108.
Chapman 1989, Biopolymers 28:1367-1382.
Chen et al., 1995, J. Biomol. Struct. & Dyn. 6:1129-1159.
Fertala et al., 1996, J. Biol. Chem. 271:14864-14869.
Fujisawa et al., 1994, Calcif. Tissue Int. 56:140-144.
Galloway 1985, In: *Biology of Invertebrate and Lower Vertebrate Collagens*, Bairoti et al., Eds., Plenum Press, New York, pp. 73-82.
Gelman et al., 1980, J. Biol. Chem. 155:8098-8102.
Helseth et al., 1979, Biopolymers 18:3005-3014.
Helseth et al., 1981, J. Biol. Chem. 256:7118-7128.
Holmes et al., 1992, Proc. Natl. Acad. Sci. USA 89:9855-9859.
Holmes et al., 1979, Biochem. Biophys. Res. Commun. 87:993-999.
Holmes et al., 1993, J. Biol. Chem. 268:15758-15765.
Hulmes et al., 1981, Proc. Natl. Acad. Sci. USA 78:3567-3571.
Hulmes et al., 1979, Nature 282:878-880.
Hulmes et al., 1985, J. Mol. Biol. 184:473-477.
Hulmes et al., 1989, J. Mol. Biol. 210:337-345.
Hulmes et al., 1995, Biophys. J. 68:1661-1670.
Jones et al., 1991, J. Mol. Biol. 218:209-219.
Kadler et al., 1987, J. Biol. Chem. 262:15696-15701.
Kadler et al., 1990, Ann. N.Y. Acad. Sci. 580:214-224.
Kadler et al., 1990, Biochem. J. 268:339-343.
Miyahara et al., 1982, J. Biol. Chem. 257:8442-8448.
Mould and Hulmes, 1982, J. Molec. Biol. 195:543-553.
Nagan et al., 1994, J. Biol. Chem. 269:22366-22371.
Parkinson et al., 1994, Physical Rev. E. 50:2963-2966.
Piez et al., 1981, Biosci. Rep. 1:801-810.
Piez, 1984, In: *Extracellular Matrix Biochemistry*, Piez et al., Eds., Elsevier, New York pp. 1-40.

(Continued)

*Primary Examiner*—Karen Cochrane Carlson
(74) *Attorney, Agent, or Firm*—Caesar, Rivise, Bernstein, Cohen & Pokotilow, Ltd.

(57) ABSTRACT

The invention relates to peptides and peptidomimetics which inhibit assembly of human type I collagen. Methods of identifying such peptides and peptidomimetics are also included in the invention.

11 Claims, 10 Drawing Sheets

OTHER PUBLICATIONS

Potschka et al., 1988, Biochemistry 27:8481-8491.
Prockop et al., 1995, Ann. Rev. Biochem. 64:403-434.
Silver et al., 1992, Proc. Natl. Acad. Sci. 89:9860-9864.
Smith 1968, Nature 219:157-158.
Veis and Payne, 1988, In: *Collagen: Biochemistry*, vol. 1, Nimni, Ed., CRC Press, Boca Raton, FL, pp. 113-138.
Vitagliano et al., 1995, J. Mol. Biol. 247:69-80.
Ward et al., 1986, J. Mol. Biol. 190:107-112.
Weiner et al., 1984, J. Am. Chem. Soc. 106:765-784.
Woodhead-Galloway, 1984, In: *Connective Tissue Matrix*, Hukins, Ed., Verlag York, Chemie, Basel, pp. 133-160.

* cited by examiner

FIG. 3A
FIG. 3B
 

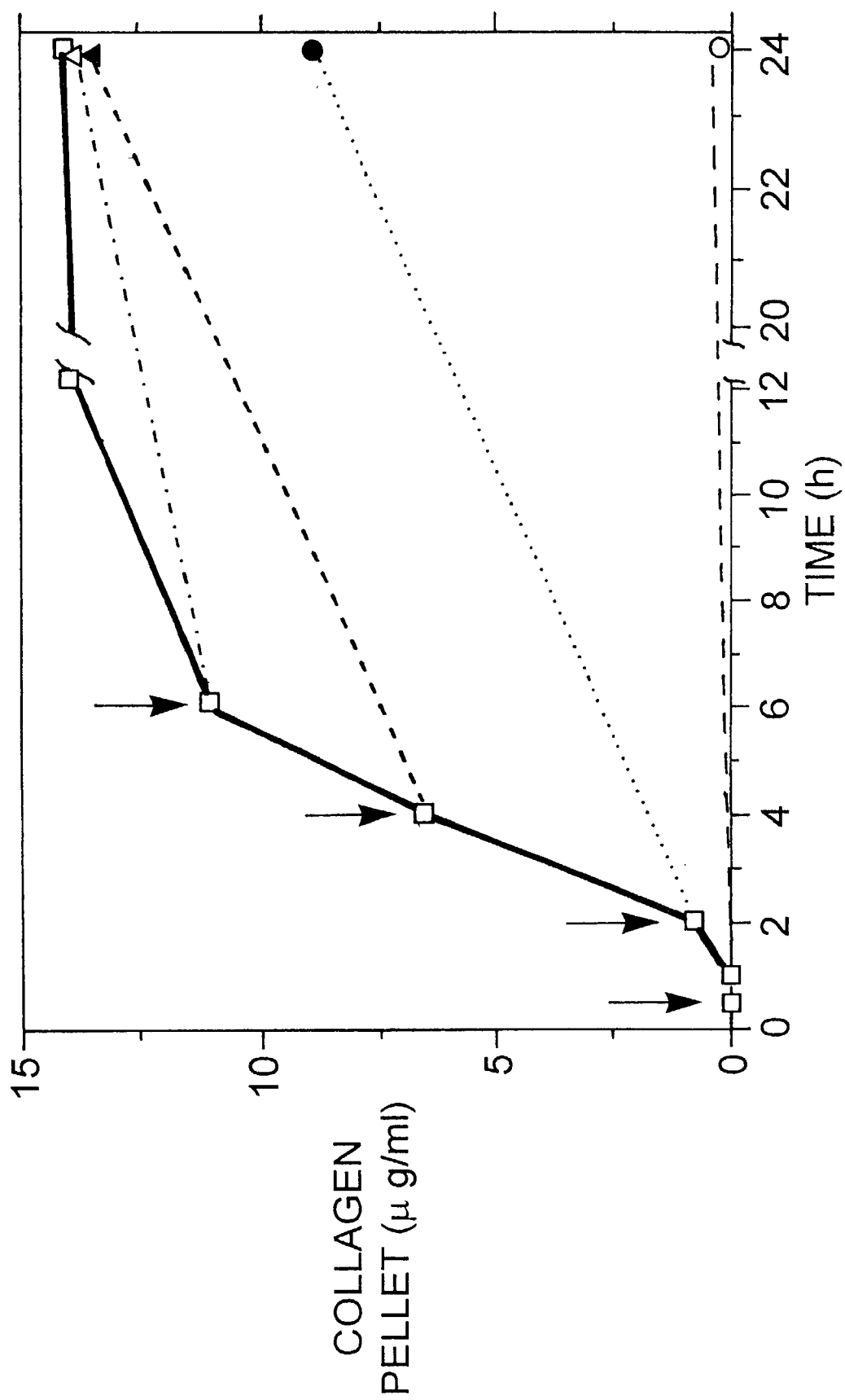

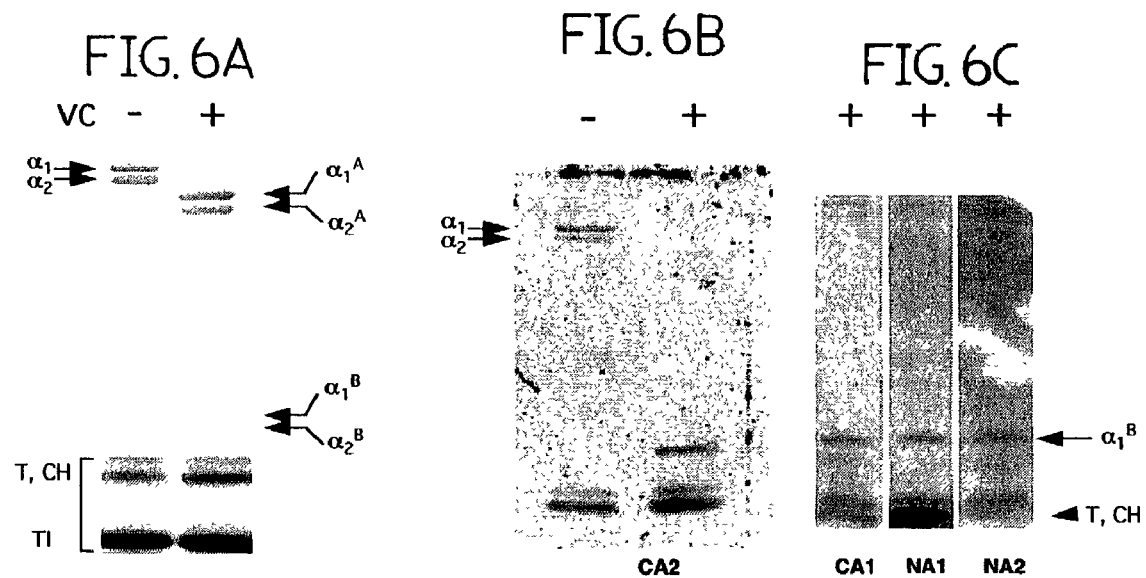

INHIBITORS OF COLLAGEN ASSEMBLY

This application is a division of U.S. patent application Ser. No. 09/517,866, filed on Mar. 3, 2000, now U.S. Pat. No. 6,472,504, which is a continuation of international Pat. application No. PCT/US98/18838, filed Sep. 10, 1998, which is entitled to priority pursuant to 35 U.S.C. 119(e) to U.S. Provisional Patent Application No. 60/058,353, filed Sep. 10, 1997. The entire disclosures of each of the three aforementioned priority documents are incorporated herein by reference.

BACKGROUND OF THE INVENTION

Fibrillar collagens form the largest protein structures found in complex organisms (Piez, 1984, In: *Extracellular Matrix Biochemistry*, Piez et al., Eds., Elsevier, New York, pp. 1–40; Prockop et al., 1995, Ann. Rev. Biochem. 64:403–434). The most abundant collagen fibrils consist almost entirely of a single monomer of type I collagen. The structure of the monomer was established several decades ago, but the precise pattern of packing of the monomer into fibrils has not been defined and remains controversial (Smith, 1968, Nature 219:157–158; Hulmes et al., 1979, Nature 282:878–880; Holmes et al., 1979, Biochem. Biophys. Res. Commun. 87:993–999; Piez et al., 1981, Biosci. Rep. 1:801–810; Hulmes et al., 1981, Proc. Natl. Acad. Sci. USA 78:3567–3571; Brodsky et al., 1982, Methods Enzymol. 82:127–173; Woodhead-Galloway, 1984, In: *Connective Tissue Matrix*, Hukins, Ed., Verlag Chemie, Basel, pp. 133–160; Hulmes et al., 1985, J. Mol. Biol. 184:473–477; Ward et al., 1986, J. Mol. Biol. 190:107–112; Galloway, 1985, In: *Biology of Invertebrate and Lower Vertebrate Collagens*, Bairoti et al., Eds., Plenum Press, New York, pp. 73–82; Chapman, 1989, Biopolymers 28:1367–1382; Jones et al., 1991, J. Mol. Biol. 218:209–219).

Type I collagen is similar to other fibrillar collagen in that it is first synthesized as a soluble procollagen containing N-propeptides and C-propeptides (Prockop et al., 1995, Ann. Rev. Biochem. 64:403–434). The propeptides are cleaved by specific N- and C-proteinases and the monomers then spontaneously assemble into characteristic fibrils. The two $\alpha 1(I)$ chains and one $\alpha 2(I)$ chains of a monomer of type I collagen are primarily comprised of about 338 repeating tripeptide sequences of -Gly-Xxx-Yyy- in which -Xxx- is frequently proline and -Yyy- is frequently hydroxyproline. The ends of the $\alpha 1(I)$ and $\alpha 2(I)$ chains consist of short telopeptides of about 11 to 25 amino acids per chain. The distribution of hydroxyproline and charged residues in the -Xxx- and -Yyy- positions in the triple-helical domain define 4.4 repeats or 4.4 D-periods of about 234 amino acids each. In longitudinal sections, the monomers are arranged in fibrils in a head-to-head-to-tail orientation with a gap of about 0.6 D-periods and, therefore, repeat of 5 D-periods. The continuity of the fibrils is maintained by many of the monomers being staggered by 1, 2, 3, or 4 D-periods relative to the nearest neighbor so as to generate gap and overlap regions. However, there are conflicting data from electron microscopy and X-ray analysis about the lateral packing of the monomers. One view is that the monomers are laterally packed in a tilted quasi-hexagonal lattice (Hulmes et al., 1979, Nature 282:878–880; Jones et al., 1991, J. Mol. Biol. 218:209–219). A related view is that the fibrils consist of "compressed" microfibrils that are comprised of monomers coiled into a rope-like pentameric structure (Smith, 1968, Nature 219: 157–158; Piez et al., 1981, Biosci. Rep. 1:801–810). Still another view is that the lateral packing of the collagen in many fibrils is either liquid-like or a biological equivalent of a liquid crystal Galloway, 1985, In: *Biology of Invertebrate and Lower Vertebrate Collagens*, Bairoti et al., Eds., Plenum Press, New York, pp. 73–82; Chapman, 1989, Biopolymers 28:1367–1382).

One experimental approach to defining the lateral packing of the monomers was to observe the initial assembly of monomers into fibrils. Early experiments (Piez, 1984, In: *Extracellular Matrix Biochemistry*, Piez et al., Eds., Elsevier, New York, pp. 1–40; Ward et al., 1986, J. Mol. Biol. 190:107–112; Veis et al., 1988, In: *Collagen: Biochemistry*, Vol. 1, Nimni, Ed., CRC Press, Boca Raton, Fla., pp. 113–138) on the re-assembly of fibrils from collagen extracted from tissues with acidic buffers suggested that the first structures formed were linear strands of monomers bound by 0.4 D-period overlaps (4 D staggers). Other observations with extracted collagens suggested the initial stages involved assembly of structures similar to pentameric microfibrils (Piez, 1984, In: *Extracellular Matrix Biochemistry*, Piez et al., Eds., Elsevier, New York, pp. 1–40; Veis et al., 1988, In: *Collagen: Biochemistry*, Vol. 1, Nimni, Ed., CRC Press, Boca Raton, Fla., pp. 113–138; Gelman et al., 1980, J. Biol. Chem. 155:8098–8102). Subsequently, a system was developed for studying assembly of type I collagen fibrils de novo by enzymic cleavage of a purified soluble precursor of procollagen under physiological conditions (Miyahara et al., 1982, J. Biol. Chem. 257:8442–8448; Kadler et al., 1987, J. Biol. Chem. 262:15696–15701; Kadler et al., 1990, Ann. N.Y. Acad. Sci. 580:214–224; Kadler et al., 1990, Biochem. J. 268:339–343). Because thick fibrils were generated in the system, it was possible to use dark-field light microscopy to follow the growth of the fibrils through intermediate stages (Kadler et al., 1990, Biochem. J. 268:339–343). The first fibrils detected had a blunt end and a pointed tip or end. Initial growth of the fibrils were exclusively from the pointed or a-tip. Later, b-tips appeared on the blunt ends of the fibrils and the fibrils grew from both directions. Scanning transmission electron microscopy indicated that both the a-tips and b-tips were near paraboloidal in shape (Holmes et al., 1992, Proc. Natl. Acad. Sci. USA 89:9855–9859 Silver et al., 1992, Proc. Natl. Acad. Sci. 89:9860–9864). Also, it appeared that the monomers are oriented with their N-termini directed toward the tips. Subsequent experiments in the same system with type II collagen suggested that the fibrils also grew from pointed tips. However, the monomers were oriented with a C-termini directed toward the tips (Fertala et al., 1996, J. Biol. Chem. 271:14864–14869). Three different models were proposed to explain the growth of fibrils from near-paraboloidal tips. One model (Silver et al., 1992, Proc. Natl. Acad. Sci. 89:9860–9864) was based on the assumption that the initial core of the fibril was a pentameric microfibril and that the fibrinl grew by addition of monomers in a helical pattern. Simulations of the model suggested that as little as two specific binding steps were required first for assembly of the microfibrillar core and then a structural nucleus with about the same diameter as the final fibril. After assembly of the structural nucleus, the fibril grew from the paraboloidal tip by addition of monomers through only one of the two binding steps. A second and related model (Hulmes et al., 1995, Biophys. J. 68:1661–1670; Hulmes et al., 1989, J. Mol. Biol. 210:337–345) suggested that assembly began with formation of an undefined inner core and then monomers were added in spiral strands to generate the near-paraboloidal tips. The second model had the advantage that it more readily than the first model accounted for X-ray diffraction data that indicated that some fraction of monomers in fibrils were laterally packed in a tilted quasi-hexagonal lattice (Hulmes et al., 1979, Nature 282:878–880; Galloway, 1985, In: *Biology of Invertebrate and Lower Vertebrate Collagens*, Bairoti et al., Eds., Plenum Press, New York, pp. 73–82). In contrast to the first two models, a third model (Parkinson et al., 1994, Physical Rev. E. 50:2963–2966) was developed in which monomers were assembled by a process involving only aggregated limited diffusion. The third model, therefore, assumed that the assembly of monomers into fibrils was similar to processes such as electrochemical depositions or perhaps formation of snowflakes, and that the process did not require the presence of specific binding sites on the monomers.

SUMMARY OF THE INVENTION

The invention relates to type I collagen assembly-inhibiting peptides. These peptides inhibit assembly of human type I collagen, for example, in an in vitro collagen self-assembly assay. In one embodiment, the peptide is selected from the group consisting of a type I collagen $\alpha$1 N-telopeptide, a type I collagen $\alpha$1 C-telopeptide, a type I collagen $\alpha$2 C-telopeptide, a type I collagen $\alpha$2 C-telopeptide derivative. By way of example, the peptide may have an amino acid sequence selected from the group consisting of SEQ ID NOs: 2, 4–11, and 13–23, preferably from the group consisting of SEQ ID NOs: 2 and 4–11, and more preferably from the group consisting of SEQ ID NOs: 4–8 and 11. In another embodiment, the peptide is a peptidomimetic of a peptide having an amino acid sequence selected from the group consisting of SEQ ID NOs: 2, 4–11, and 13–23.

The invention also relates to a method of identifying a type I collagen assembly-inhibiting peptide. This method comprises immobilizing a collagen species on a support. The collagen species is selected from the group consisting of human type I collagen and a human type I collagen peptide. The support is contacted with a labeled peptide in the presence or absence of an unlabeled test peptide. The labeled peptide is known to inhibit collagen self-assembly. The amount of labeled peptide bound to the support is assessed, and a lower amount of labeled peptide bound to the support in the presence of the test peptide compared with the level of binding of the labeled peptide to the support in the absence of the test peptide is an indication that the test peptide is a type I collagen assembly-inhibiting peptide.

The invention further relates to a method of identifying a type I collagen assembly-inhibiting peptide. This method comprises immobilizing a collagen species on a support. Again, the collagen species is selected from the group consisting of human type I collagen and a human type I collagen peptide. The support is contacted with at least one peptide-bearing particle which comprises a test peptide. It is then assessed whether the peptide-bearing particle binds with the support. Binding of the peptide-bearing particle to the support is an indication that the test peptide is a type I collagen assembly-inhibiting peptide. In one embodiment of this method, the human type I collagen peptide has the amino acid sequence of amino acid residues 776 through 796, inclusive, of the $\alpha$1 chain of human type I collagen. In another embodiment, the peptide-bearing particle is a phage or a phage display peptide library. In a variation of this method, the support is rinsed prior to assessing whether the peptide-bearing particle binds with the support. In one embodiment of this method assessing whether the peptide-bearing particle binds with the support comprises contacting the support with a collagen un-binding eluent and detecting the presence of the peptide-bearing particle in the eluent. By way of example, the collagen un-binding eluent may be selected from the group consisting of Tris-glycine buffer at a pH of about 2.2, a suspension comprising human type I collagen, and a suspension comprising a peptide having the amino acid sequence of amino acid residues 776 through 796, inclusive, of the $\alpha$1 chain of human type I collagen. In one embodiment of this method, the peptide-bearing particle is a phage, and detecting the presence of the phage comprises detecting the ability of the phage to lyse cultured cells. In another variation of this method, the peptide-bearing particle in the eluent is contacted with a second support, wherein the second support has the same or a different collagen species immobilized thereon.

The invention also relates to a method of inhibiting type I collagen self-assembly comprising contacting the collagen with a type I collagen assembly-inhibiting peptide. In one embodiment, the collagen is in a human.

The invention also relates to use of a type I collagen assembly-inhibiting peptide for preparation of a medicament for inhibiting type I collagen self-assembly in an animal, preferably in a human.

The invention also relates to a chromatographic medium comprising a support having a type I collagen assembly-inhibiting peptide immobilized thereon.

The invention further relates to a method of purifying human type I collagen. This method comprises contacting a relatively impure suspension comprising human type I collagen with a support having a type I collagen assembly-inhibiting peptide immobilized thereon and separating the support from the suspension to yield relatively purified human type I collagen.

BRIEF DESCRIPTION OF THE DRAWINGS

FIG. 2, comprising

FIG. 3, comprising FIGS. 3A and 3B is a pair of dark field images of collagen I fibrils. pCcollagen was incubated with C-proteinase at 37° C. for 24 hours in a sealed chamber in the presence (+) or absence (−) of 2.5 mM F3 peptide. Fibrils were photographed using microscope with Dark field attachment. In these Figures, the magnification was 300×.

FIG. 4 is a graph which indicates the effects of adding the peptide F3 at varying time points during fibril assembly. The open squares denote fibril assembly under control conditions. Arrows indicate times when 2.5 mM of peptide F3 was added to parallel samples, whereafter incubation was continued for 24 hours.

FIG. 5, comprising In FIG. 5A, the electroblot assay was performed using biotinylated C-telopeptide of the α1 chain of human type I collagen. In FIG. 5B, the electroblot assay was performed using biotinylated C-telopeptide of α2 chain of human type I collagen. In FIG. 5C, the electroblot assay was performed using biotinylated N-telopeptide of the α1 chain of human type I collagen. In FIG. 5D, the electroblot assay was performed using biotinylated N-telopeptide of α2 chain of human type I collagen.

FIG. 6, comprising FIGS. 6A, 6B, and 6C, is a trio of images of assays which depict binding of biotinylated telopeptides to collagenase A and B fragments of type I collagen. FIG. 6A is a Coomassie Brilliant Blue-stained polyacrylamide gel electrophoretic assay which demonstrates the presence of α1(I), α2(I) chains fragments with and without vertebrate collagenase treatment. FIGS. 6B and 6C are filter electroblot assays performed using biotinylated telopeptides. In these two figures, "+" indicates samples which were treated with vertebrate collagenase prior to electroblotting, and "−" indicates samples which were not treated with vertebrate collagenase. In each of FIGS. 6A, 6B, and 6C, "T" and "CH" refer to bands corresponding to trypsin and chymotrypsin, respectively, which were used to convert the procollagen into collagen.

FIG. 7, comprising

FIG. 9, comprising In FIG. 9A, competition for binding of the biotinylated C-propeptide of the α1(I) chain (peptide F2) is assayed. In FIG. 9B, competition for binding of the C-telopeptide from the α2(I) chain (peptide F3).

FIG. 10, comprising In FIG. 10A hydrophobic residues are displayed. In FIG. 10B electrostatic charges are displayed, red indicating positive charge and purple indicating negative charge. α1-Arg 780, α1-Val 783, and α-Arg 792 are shown to indicate possible regions of interaction.

DETAILED DESCRIPTION OF THE INVENTION

Figure 1:
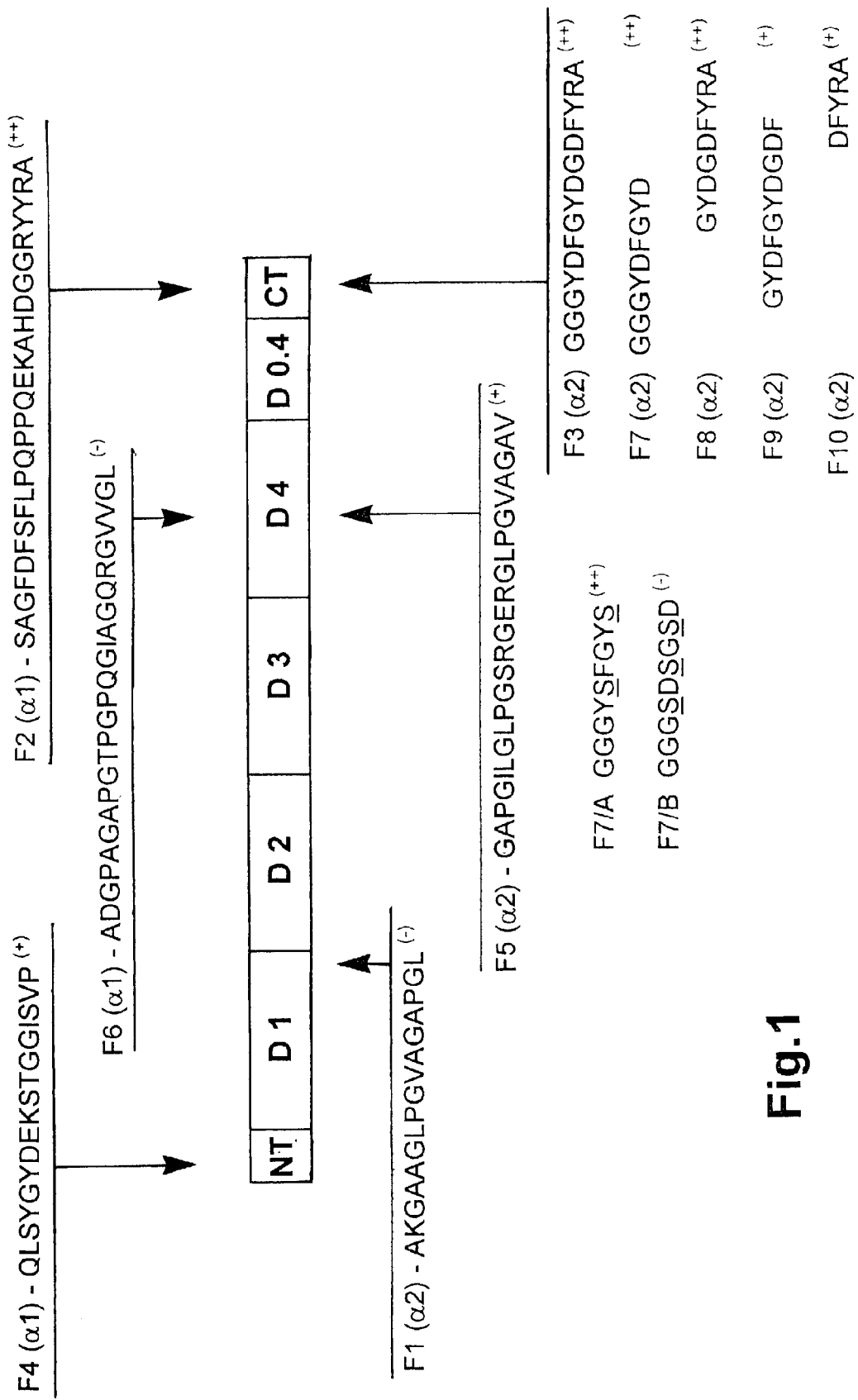
FIG. 1 is a schematic of the structure of a type I procollagen molecule divided into D periods, N-telopeptides and C-telopeptides. Sequences above and below the model indicate the effect of peptides having the indicated sequence as inhibitors of fibril assembly. The symbols used are as follows: (−), no effect on fibri assembly; (+), about 50% inhibition of fibril assembly at a peptide concentration of 2.5 mM; and (++), complete inhibition of fibril assembly at a peptide concentration of 2.5 mM. "NT" refers to N-terminal telopeptides, and "CT" refers to C-terminal telopeptides.

It has been discovered according to the present invention that self-assembly of collagen may be inhibited by specific peptides and peptidomimetics derived from these peptides. These peptides and peptidomimetics are herein referred to as type I collagen assembly-inhibiting peptides. The present discovery thus provides a heretofore unknown class of compounds which are useful as anti-fibrotic compounds, which are useful in the prevention of metastasis of tumors, and are also useful in a variety of other applications.

The present invention is based on the discovery that collagen telopeptides bind to a specific site in the major triple-helical domain of the collagen monomer. It has been discovered that both the specificity and the affinity of this binding is unexpected in that, as the data presented herein establish, the process of self-assembly of collagen into fibrils is completely inhibited in the presence of these telopeptides. Data are presented herein which comprise the results of a number of experiments on a number of telopeptides, and while several telopeptides function to inhibit collagen self-assembly into fibrils, the C-terminal telopeptide of the α1(I) chain had the highest dissociation constant, this being $4 \times 10^{-6}$ M.

As the data presented herein also establish, it has been possible to model both the telopeptide binding site in the collagen triple helix and the collagen binding site in one of the telopeptides. This modeling provides detailed information for use in designing additional peptides and peptidomimetics which inhibit self-assembly of collagen. Once the sequence of a functional peptide is known (in the present situation, the functional peptide is an inhibitor of collagen self-assembly), the designing of other compounds having the same property by computer modeling is now commonplace in the pharmaceutical sciences. Thus, based on the present discovery, a collagen self-assembly inhibitory peptide may be modified to generate an infinite variety of potential compounds that may have improved activity compared with the first discovered compound. The invention thus contemplates the use of the information provided herein for the development of other peptides and peptidomimetics for use as inhibitors of collagen self-assembly.

In addition, peptides other than those described herein may be generated using combinatorial phage display libraries which express proteins on their surface, or by using other recombinant DNA libraries. For example, to isolate additional peptides using a phage display library, a collagen fragment of about 20 amino acids identified in the collagen triple helix as a major telopeptide binding site, is immobilized on a solid surface. In a parallel assay, the telopeptide to which collagen binds is also immobilized. Recombinant phage which display the recombinant protein on their surface are added to the immobilized protein fragments under conditions which would ordinarily promote binding of the telopeptide to the collagen fragment. Phage which bind the collagen fragment are isolated, DNA is extracted therefrom, and DNA encoding the peptide which binds the collagen fragment is isolated and sequenced. Peptides encoded by the DNA are then isolated by expression of the DNA in any ordinary expression system. Alternatively, once the sequence of a collagen binding peptide is known, the peptides may be generated synthetically in a peptide synthesizer.

Antibodies which bind the telopeptide binding site in collagen may also be isolated using phage display libraries. Essentially, an antibody-expressing phage display library is added to the immobilized collagen fragment under conditions to promote binding of the antibody to the collagen fragment. Phage which bind to the collagen fragment are subsequently isolated, and the antibody expressed thereby is obtained and sequenced.

There are a variety of phage display libraries that are commercially available which may be used in the procedure just described for the generation of collagen binding peptides capable of inhibiting assembly of collagen. It is also possible, using analogous methods, to use commercially-available or specially-made cell display libraries, such libraries comprising cells having at least one peptide present on their surface and able to contact a medium in which the cell is suspended.

The invention also includes peptides which are homologous to the peptides disclosed herein which function to inhibit collagen self-assembly.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two peptide molecules is occupied by cysteine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the amino acid sequences Lys-Pro-Cys-Arg and Met-Pro-Cys-Gly share 50% homology.

The invention includes an isolated human type I collagen assembly-inhibiting peptide capable of inhibiting self-assembly of collagen. Preferably, the amino acid sequence of such an isolated peptide is about 70% homologous, more preferably about 80% homologous, even more preferably about 90% homologous, more preferably, about 95% homologous, and most preferably, at least about 99% homologous to the amino acid sequence of the α1(I) C-terminal peptide disclosed herein. Given the similarity among the amino acid sequences of type I collagen proteins of various animals, particularly mammals, it is understood that the type I collagen assembly-inhibiting peptides of the invention may be used to inhibit self-assembly of type I collagen in a variety of animals, particularly mammals.

Substantially pure type I collagen assembly-inhibiting peptide obtained as described herein may be purified by following known procedures for protein purification, wherein an immunological, enzymatic or other assay is used to monitor purification at each stage in the procedure. Alternatively, the peptide may be generated synthetically.

As used herein, the term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

The present invention also provides for analogs of peptides which are capable of inhibiting collagen self-assembly. Analogs can differ from naturally occurring proteins or peptides by conservative amino acid sequence differences or by modifications which do not affect sequence, or by both.

For example, conservative amino acid changes may be made, which although they alter the primary sequence of the peptide, do not normally alter its function. Conservative amino acid substitutions typically include substitutions within the following groups:
glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are peptides which have been modified using ordinary molecular biological techniques so as to improve their resistance to proteolytic degradation or to optimize solubility properties. Analogs of such peptides include those containing residues other than naturally occurring L-amino acids, e.g., D-amino acids or non-naturally occurring synthetic amino acids. The peptides of the invention are not limited to products of any of the specific exemplary processes listed herein, in that the invention includes any peptides isolated using the procedures described herein which have the biological activity of the α1(I) peptide disclosed herein.

The peptide will ordinarily be at least about four contiguous amino acids, typically at least about four to about eight contiguous amino acids, more typically at least about four to about twelve contiguous amino acids, usually at least about four to about twenty contiguous amino acids, and typically at least about four to about twenty or more contiguous amino acids in length.

A "collagen assembly inhibitory peptide" is one which when added to a preparation of collagen monomers, inhibits the formation of collagen fibrils.

A collagen assembly inhibitory peptide is "biologically active" if it is capable of inhibiting collagen self-assembly in any one of the assays described herein. For example, in a high throughput assay described herein in the description of the data shown in FIGS. 8 and 9, a series of wells in a microtiter plate are coated with monomeric collagen. An amount of HCl is added to each well and the plates are dried. The plates are rinsed in buffer and bovine serum albumin (BSA) is added to block non-specific binding sites on the collagen. Samples containing labeled peptide (for example, biotinylated peptide) which is known to inhibit collagen self-assembly and unlabeled test peptide at various concentrations are premixed and are added to the wells. Peptides which do not bind collagen serve as negative controls. The wells are incubated for a period of time, the plates are washed and streptavidin conjugated to alkaline phosphatase is added. Incubation is continued for a further period of time following which a developing reagent is added to the wells. The amount of binding of the labeled peptide to the collagen is assessed and the degree of inhibition of binding by the test peptide is also assessed. Any test peptide which inhibits binding of the labeled peptide is isolated and is tested further for the ability to inhibit collagen self-assembly in the assays described herein in the description of FIGS. 1, 2 and 3.

It will be appreciated that the assay of the invention is not limited to the particular components recited herein. Rather, assays which comprise immobilized variants or fragments of collagen, assays which comprise phage which display collagen assembly inhibitory peptides, and assays which include other means of assessing the competition for binding known versus test fragments to collagen i.e., assays which employ alternative labeling/detection systems, are also contemplated as part of the invention.

The above described assays and those described in detail herein in the experimental examples section are also applicable to peptidomimetics having the ability to inhibit the self-assembly of collagen. Peptidomimetics may be generated using techniques described in PCT/US93/01201 and in U.S. Pat. No. 5,334,702.

The invention includes methods of identifying type I collagen assembly-inhibiting peptides. One such method involves immobilizing a collagen species such as human type I collagen or a human type I collagen peptide on a support. A labeled peptide which is known to bind to the collagen species is contacted with the support, as is an unlabeled test peptide. If the test peptide binds to the collagen species, then binding of the labeled peptide to the support will be decreased, resulting in less association of the label with the support and greater retention of label in the medium surrounding the support. Substantially any label (e.g. a radionuclide) which may be attached to a peptide may be used in this method.

An alternate method of identifying a type I collagen assembly-inhibiting peptide is described in greater detail in Example 2 herein. Briefly, a collagen species is immobilized on a support, as described herein. At least one peptide-bearing particle which comprises a test peptide is contacted with the support. If the test peptide is a type I collagen assembly-inhibiting peptide, then the peptide-bearing particle with bind with the support. The support may be rinsed, for example, with a solution (e.g. phosphate-buffered saline) which will not cause type I collagen assembly-inhibiting peptides to desorb from the support. In order to desorb such peptides from the support, a collagen un-binding eluent may be contacted with the support. A collagen un-binding eluent is any composition which will cause a type I collagen assembly-inhibiting peptide to desorb from the collagen species. Examples of collagen un-binding eluents include, but are not limited to, Tris-glycine buffer at a pH of about 2.2, a suspension comprising human type I collagen, and a suspension comprising a peptide having the amino acid sequence of amino acid residues 776 through 796, inclusive, of the α1 chain of human type I collagen. Examples of peptide-bearing particles which may be used according to this method include phage display peptide libraries and cell surface display peptide libraries, both of which are known in the art.

As used herein, a "human type I collagen peptide" is a polypeptide having an amino acid sequence homologous with at least a portion of human type I collagen, but being shorter in length than human type I collagen. An example of a human type I collagen peptide is the α1-776–796 peptide described herein.

Peptides or peptidomimetics which inhibit the assembly of collagen may be formulated so as to be suitable for administration to a mammal in need of such inhibitors. The peptide or peptidomimetic is prepared for administration by being suspended or dissolved in a pharmaceutically acceptable carrier such as saline, salts solution or other formulations apparent to those skilled in the art of administration of peptides and peptidomimetics. The compositions of the invention may be administered to a mammal in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema) or nasally (e.g., by nasal spray). The appropriate pharmaceutically acceptable carrier will be evident to those skilled in the art and will depend in large part upon the route of administration and the age and type of mammal being treated.

Protocols for treatment of mammals involving administration of a peptide or peptidomimetic of the invention, will be apparent to those skilled in the art and will vary depending upon the type of disease the type and age of the mammal. Treatment regimes which are contemplated include a single dose or dosage which is administered hourly, daily, weekly or monthly, or yearly. Dosages may vary from 1 μg to 1000 mg/kg of body weight of the peptide or peptidomimetic and will be in a form suitable for delivery of the compound. The route of administration may also vary depending upon the disorder to be treated.

In some instances, it may be necessary to ensure that the peptide or peptidomimetic is administered to a localized site in the mammal and that the peptide or peptidomimetic is prevented from diffusing to other sites in the mammal. In such instances, the peptide or peptidomimetic may be administered to the mammal in an enclosed yet porous device wherein the peptide is effectively prevented from diffusing away from the site of administration.

Additional information describing administration of peptidomimetics is provided in PCT/US93/01201 and U.S. Pat. No. 5,334,702, which are hereby incorporated herein by reference. Any of the techniques described in either of these two references may be employed in the present invention for the administration of peptidomimetics.

One skilled in the art will appreciate, in view of the present disclosure, that the human type I collagen assembly-inhibiting peptides of the invention may be used to inhibit collagen self-assembly both in vitro and in vivo. Thus, for example, the peptides of the invention may be administered to a human to inhibit type I collagen assembly in the human. The peptides may be administered to the human in the form of a medicament comprising at least one peptide of the invention.

A problem that has been recognized by those who produce collagen ex vivo (i.e. recombinant collagen) is that it is difficult to devise a large-scale method for concentrating and purifying recombinant collagen. Because, as described herein, the type I collagen assembly-inhibiting peptides of the invention bind to human type I collagen, these peptides may be used to make a chromatographic medium suitable for large-scale purification or concentration of human type I collagen. This chromatographic medium comprises a support having at least one type I collagen assembly-inhibiting peptide of the invention immobilized thereon. Substantially any of the numerous art-recognized methods of immobilizing a peptide on a support may be used to make the medium, with the proviso that it is necessary that at least some of the peptide must be available to contact a solution surrounding the medium, so that collagen suspended in the solution may contact, and bind to, the peptide. The chromatographic medium may be used, for example to purify recombinant human type I collagen. To do so, a relatively impure suspension comprising human type I collagen is contacted with the support. Collagen in the suspension thereby binds to peptide immobilized on the support. The suspension is then separated from the support, for example by rinsing the support with a solution which does not comprise the suspension. Human type I collagen is thereby relatively purified. If desired, the collagen may be desorbed from the support by contacting the support with a solution in which collagen does not bind with the peptide. Examples of such solutions include, for example, Tris-glycine buffer at a pH of about 2.2.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Design and Synthesis of Peptides

To design peptides, we have referred to the 1D stagger model for the collagen monomer organization in the fibril (FIG. 1). Six parent peptides were designed to interact with hydrophobic regions on the collagen I monomer. Three of the peptides (F1, F5 and F6) contained sequences found in the triple-helical region of the molecule, and three of the peptides (F2, F3 and F4 had sequences found in non-helical telopeptides. The peptides were commercially synthesized and purified. Homogeneity and stability of the peptides in experimental conditions were assayed by reverse-phase HPLC. All the peptides were freely soluble in the fibril formation buffer. pH of peptide solutions was monitored with a solid state micro-pH electrode (Beckman).

Assay of Fibril Assembly

Assembly of collagen I into fibrils de novo was assayed under conditions employed previously (Miyahara et al., 1982, J. Biol. Chem. 257:8442–8448; Kadler et al., 1987, J. Biol. Chem. 262:15696–15701; Kadler et al., 1990, Ann. N.Y. Acad. Sci. 580:214–224; Kadler et al., 1990, Biochem. J. 268:339–343; Fertala et al., 1996, J. Biol. Chem. 271: 14864–14869). In brief, $^{14}C$-labeled type I procollagen was recovered from the medium of cultured human skin fibroblasts and was purified with two chromatographic steps to homogeneity. The type I procollagen was processed to pccollagen I by cleavage with procollagen N-proteinase purified from organ cultures of chick embryo tendons. "pCcollagen" is a partially processed procollagen which is missing the N-terminal telopeptide, but which retains the C-terminal telopeptide. The pCcollagen was then isolated on a gel filtration column. Fibril assembly was assayed in a 20 ml reaction volume in a 250 ml plastic centrifuge tube sealed with a plunger and containing a physiological bicarbonate buffer, 30 mg/ml pCcollagen I, and 15 units/ml procollagen C-proteinase purified from chick embryo tendons. Potentially inhibitory peptides were added to the reaction mixture to final concentrations of 0.5 to 2.5 mM in 5 ml of buffer. After incubation for 0.5 to 24 hours at 37° C., the sample was centrifuged 13,000×g for 10 min. The pellet and supemate fractions were separated by electrophoresis on a 7.5% polyacrylamide gel in SDS and the gel assayed either with a phosphor storage imager (Molecular Dynamics) or by staining with colloidal Coomassie blue (Brilliant Blue, Sigma) and analysis with a densitometer (Personal Densitometer, Molecular Dynamics). Alternatively, the reaction was carried out in a sealed chamber on a microscopic slide and followed by Dark field light microscopy (Zeiss model 009).

Localization of Binding Sites on Collagen Filters

Type I collagen extracted with 0.5 M acetic acid from mouse skin was digested with pepsin, and the a chains separated by gel electrophoresis in SDS. To generate CNBr peptides, gel slices containing α1(1) and α2(I) chains were placed into tubes and a chains were digested with 10 mg/ml or 200 mg/ml CNBr in 70% formic acid at room temperature overnight. The gel slices were equilibrated with 0.05 mM Tris-HCl buffer (pH 6.8) over 3 hours. Gel pieces containing CNBr peptides derived from individual collagen a chains were transferred into the wells of the second gel prepared with a 6% polyacrylamide stacking gel and 12% polyacrylamide separating gel with 0.5 M urea. After electrophoresis, the gel was electroblotted overnight at 4° C. onto a nitrocellulose filter (Millipore). To study binding of telopeptides to collagen fragments, the method described by Fujisawa et al. (Fujisawa et al., 1994, Calcif. Tiss. Int. 56:140–144) was used. The filters were blocked with 1% bovine serum albumin (Sigma) and then incubated overnight with 20 ml of 5 mg/ml peptide that was substituted at the N-terminus with biotin (synthesized for us by American Peptide Company, Inc.). The filter was washed three times with Tris-buffered saline containing 0.02% Tween (TBST) and incubated 30 min with a 1:30,000 dilution of horseradish peroxidase conjugated with avidin (Sigma). The bands were detected by chemiluminescence (ECL; Amersham) after exposure to an X-ray film for 3 to 10 min.

To generate vertebrate collagenase fragments, 3 mg of type I pccollagen from cultured human fibroblasts was cleaved with 10 mg/ml of vertebrate collagenase from cultured rat skin fibroblasts (generous gift from John J. Jeffrey, Department of Medicine, Albany Medical College) for 3 hours at 25° C. in a volume of 40 ml of 50 mM Tris-HCl, 10 mM CaCl2 and 100 mM NaCl, pH 7.4. To remove the C-propeptide, 2 ml of a mixture of trypsin (1 mg/ml) and chymotrypsin (2.5 mg/ml) in the same buffer was added, and the sample was incubated at 20° C. for 2 min. The reaction was stopped with 0.5 mg/ml soybean trypsin inhibitor (Sigma). The sample was then separated by electrophoresis on a 10% polyacrylamide gel in SDS and processed with the same protocol as the CNBr fragments.

To define the telopeptide binding site with a competitive assay, 96-well titiation plates (Immulon 3, Dynatech Laboratories, Inc.) were used. Seventy microliters of the solution containing 3 mg of monomeric collagen (Vitrogen 100, Collagen Biomaterials) in 0.01 N HCl was added to each well, and the plates were dried at room temperature. The plates were rinsed with sterile phosphate buffered saline and non-specific binding sites were blocked with 1% bovine serum albumin. For the competition assay, pre-mixed samples were prepared that contained 50 mM biotinylated F2 or F3 peptide with 10 to 500 mM peptide α1-776/797. As a negative control, peptide α2-218/233 was used at concentrations from 10 to 500 mM. The peptide mixtures were added into wells containing immobilized collagen and the samples incubated at 25° C. for 12 h. The plates were washed with PBS containing 0.05% Tween. To detect biotinylated peptides bound to collagen surface, streptavidin conjugated to alkaline phosphatase (BioRad) was added at 1:20,000 dilution. After 2 hours of incubation, the plates were washed with phosphate buffered saline (PBS) containing 0.05% Tween, and developing reagent 3 mM p-nitrophenyl phosphate in 0.05 M $Na_2CO_3$, 0.05 mM $MgCl_2$, pH 9.5, was added. After 2 hours of incubation, the reaction was measured with microtiter plate reader (Dynatech Laboratories) using a 405 nanometer filter.

Computer Modeling of Binding Sites

Figure 2A:
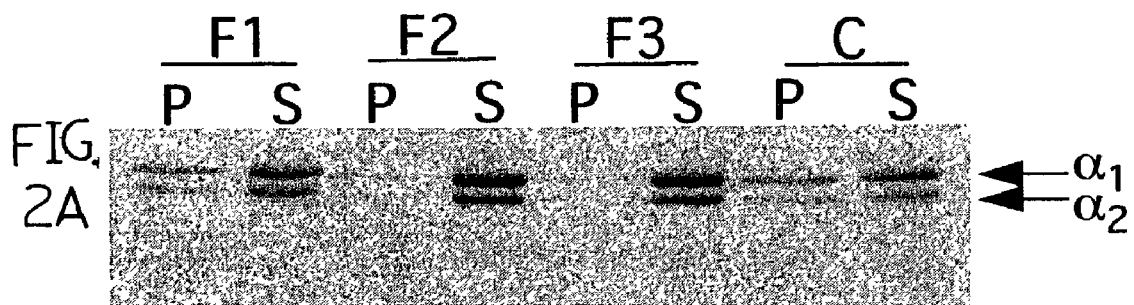
FIGS. 2A, 2B, and 2C, is a pair of images of SDS-PAGE gels which demonstrate fibril formation in the presence of synthetic peptides. In each of FIGS. 2A, 2B, and 2C, $^{14}$C-Labeled pCcollagen I (30 mg/ml) was incubated with C-proteinase (15 units/ml) for 24 hours at 37° C. F1, F2, F3, F4, F5, and F6 peptides were added to the reaction mixture at concentrations of 2.5 mM. Fibrils were separated from collagen monomers by centrifugation and analyzed by gel electrophoresis in SDS. In each instance, "P" indicates to the pellet fraction and "S" indicates the supernatant fraction. Sample "C" control sample, and sample "SC/F3" was performed using a peptide having the same amino acid residues as F3, but in a scrambled order (YGAGFDDGDYGYRYG).
Figure 2B:
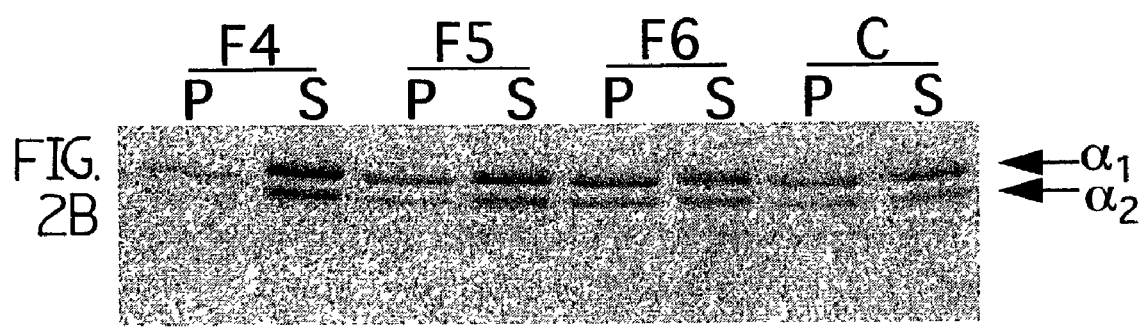
Figure 2C:
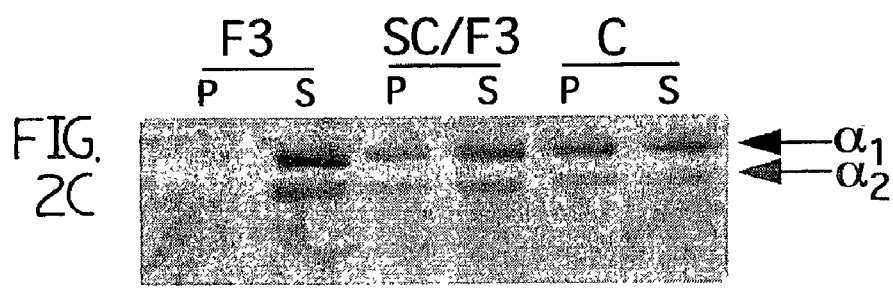
Figure 5A:
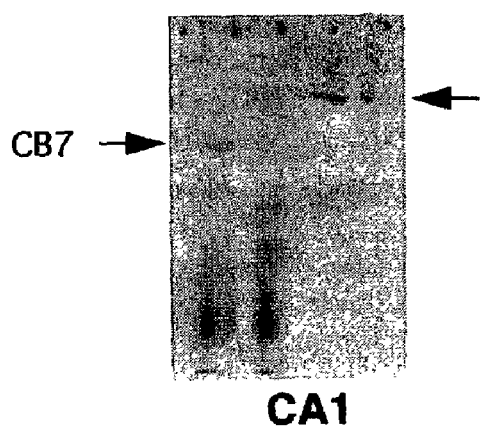
FIGS. 5A, 5B, 5C, and 5D, is a quartet of images of electroblot assays. Binding of biotinylated telopeptides to the α1(I) chain and the CB7 fragment chain. The α1(I) and α2(I) chains of type I collagen or CNBr fragments of the chains were separated by polyacrylamide gel electrophoresis and electroblotted onto filters. The filters were then hybridized with a biotinylated telopeptide followed by assay of the washed filter with streptavidin-horseradish peroxidase. "CNBr+" indicates α1(I) or α2(I) chains which were digested with cyanogen bromide.
Figure 5B:
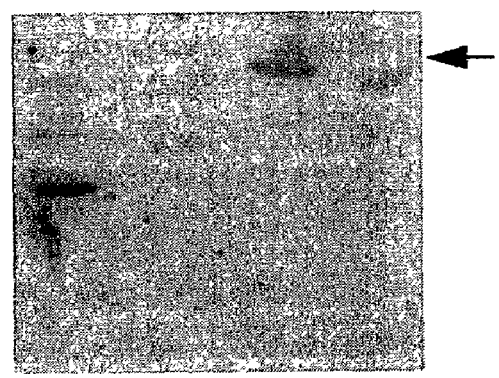
Figure 5C:
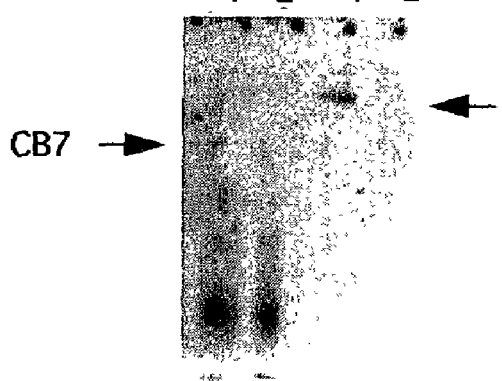
Figure 5D:
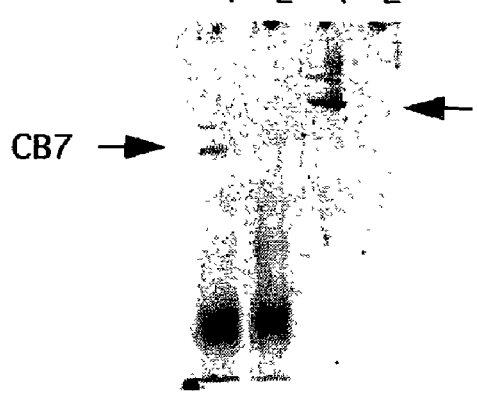

Molecular modeling was performed on a Silicon Graphic (Indigo 2) computer system using the SYBYL software package, version 6.3 (Tripos, Inc.). The model of the collagen I triple helix fragment including sequence from α1-766/801 and α2-766/801 was carried out as described by Chen et al. (1995, J. Biomol. Struct. & Dyn. 6:1129–1159). The model of F7 peptide was created using SYBYL/Biopolymer module. All the models were energy minimized using a conjugate gradient method and subject to repeating cycles of molecular dynamics using Kollman force field and united atoms (Weiner et al., 1984, J. Am. Chem. Soc. 106:765–784). To analyze interaction of F7 peptide with the collagen I binding region, intermolecular energy of interaction was analyzed to identify possible binding conformations. Surface calculations, lipohelicity potential, and electrostatic potential of the molecules were analyzed using SYBYL/Molcad module.

that none of the peptides were degraded under experimental conditions used here (data not shown). The peptides were added in concentrations of 2.5 mM to the system for assaying fibril formation by the cleavage of pCcollagen with C-proteinase (Miyahara et al., 1982, J. Biol. Chem. 257: 8442–8448; Kadler et al., 1987, J. Biol. Chem. 262:15696–15701; Kadler et al., 1990, Ann. N.Y. Acad. Sci. 580:214–224; Kadler et al., 1990, Biochem. J. 268:339–343; Fertala et al., 1996, J. Biol. Chem. 271:14864–14869). As indicated in FIG. 2 and Table I, the peptides F1 and F6 caused little if any inhibition of fibril assembly. Peptides F2, F3 and F4 almost completely inhibited fibril assembly, whereas F5 inhibited assembly by about 50% under the conditions of the experiment. Inhibition of fibril assembly with the peptide F3 was directly demonstrated by following the reaction in a sealed chamber with Dark field light microscopy. No fibrils appeared when F3 was present in a concentration of 2.5 mM (FIG. 3, right panel). The specificity of the effects was demonstrated by preparing a peptide in which the same amino acids found in F3 were assembled in a random sequence. As indicated in FIG. 2B, the peptide with the scrambled sequence (SC/F3) had no effect on fibril assembly. Assays in which the concentration of the peptide F3 were varied indicated that fibril assembly was inhibited about 40% with a concentration of about 1.5 mM and almost 100% with 2.5 mM (Table I).

TABLE I

| Peptide | | | | Fibril Assembly | |
| --- | --- | --- | --- | --- | --- |
| Region of Sequence | Code | Amino Acid Sequence | SEQ ID NO: | Concentration | % Inhibition |
| α2-217/233 | F1 | AKGAAGLPGVAGAPGL | 1 | 2.5 mM | 5 |
| α2-778/801 | F5 | GAPGILGLPGSRGERGLPGVAGAV | 2 | 2.5 mM | 50 |
| α1-761/785 | F6 | ADGPAGAPGTPGPQGIAGQRGVVGL | 3 | 2.5 mM | 0 |
| α1 N-telopeptide | F4 | QLSYGYDEKSTGGISVP | 4 | 2.5 mM | 90 |
| α1 C-telopeptide | F2 | SAGFDFSFLPQPPQEKAHDGGRYYRA | 5 | 2.5 mM | 95 |
| α2 C-telopeptide | F3 | GGGYDFGYDGDFYRA | 6 | 2.5 mM | 95 |
| α2 C-telopeptide | F3 | GGGYDFGYDGDFYRA | 6 | 2.0 mM | 70 |
| α2 C-telopeptide | F3 | GGGYDFGYDGDFYRA | 6 | 1.5 mM | 45 |
| α2 C-telopeptide | F3 | GGGYDFGYDGDFYRA | 6 | 0.5 mM | 25 |
| α2 C-telo Derivative | F7 | GGGYDFGYD | 7 | 2.5 mM | 90 |
| α2 C-telo Derivative | F8 | GYDGDFYRA | 8 | 2.5 mM | 90 |
| α2 C-telo Derivative | F9 | GYDFGYDGDF | 9 | 2.5 mM | 70 |
| α2 C-telo Derivative | F10 | DFRYRA | 10 | 2.5 mM | 70 |
| α2 C-telo Derivative | F7/A | GGGYSFGYS | 11 | 2.5 mM | 90 |
| α2 C-telo Derivative | F7/B | GGGSDSGSD | 12 | 2.5 mM | 0 |

Assays of Inhibition of Fibril Formation with Synthetic Peptides

Six synthetic peptides (FIG. 1) were prepared on the basis of two general considerations: (1) Extensive previous work (see refs. 1 and 2) had demonstrated that the telopeptides were required to be present on the monomers in order to generate tightly packed fibrils; and (2) the self-assembly of collagen monomers is entropy driven (Kadler et al., 1987, J. Biol. Chem. 262:15696–15701) and, therefore, any specific binding sites in the triple helix are likely to be found in hydrophobic sequences. As indicated in FIG. 1, one peptide (F6) contained relatively hydrophobic sequences found near the end of D1 period of the α2(I) chain, second peptide (F5) had hydrophobic sequences found near the middle of the D4 period of the α2(I) chain. F6 contained sequences that spanned the vertebrate collagenase cleavage site of -Gly-le- in the D4 period of the α1(I) chain. The remaining three peptides had the sequences of the α2-N-, α1 and α2 C-telopeptides. Assays by reverse-phase HPLC demonstrated The Peptide F3 Inhibits Fibril Assembly if Added to the Lag Phase and Early Propagation Phase but not Later in the Assembly Process To define the kinetics for inhibition of fibril assembly by the telopeptides, the peptide F3 was added in a concentration of 2.5 mM during the lag phase, early propagation phase, mid-propagation phase, or late propagation phase of fibril assembly (FIG. 4). The peptide inhibited fibril formation if added during the lag period. It had little of any effect if added during the mid-propagation phase of fibril assembly.

Location of the Telopeptide Binding Site in the Triple Helix of Type I Collagen

Figure 7A:
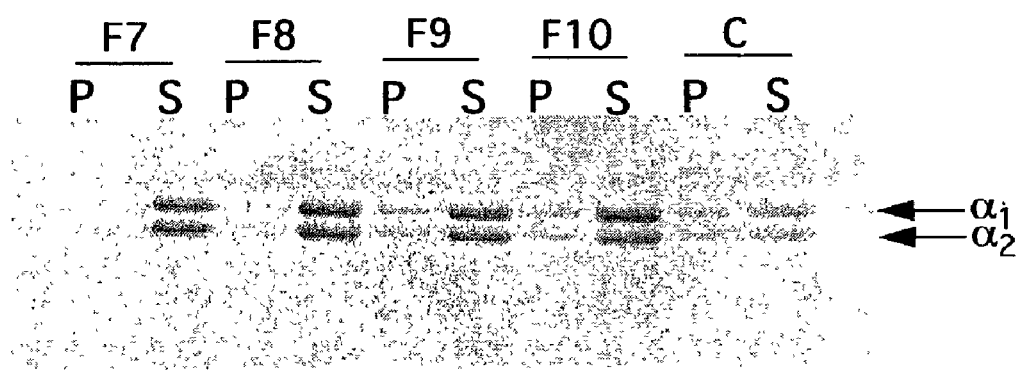
FIGS. 7A and 7B, is a series of assays for inhibition of fibril formation using peptides that are fragments and modified version of the α2-C-telopeptide (F3), as described herein.
Figure 7B:
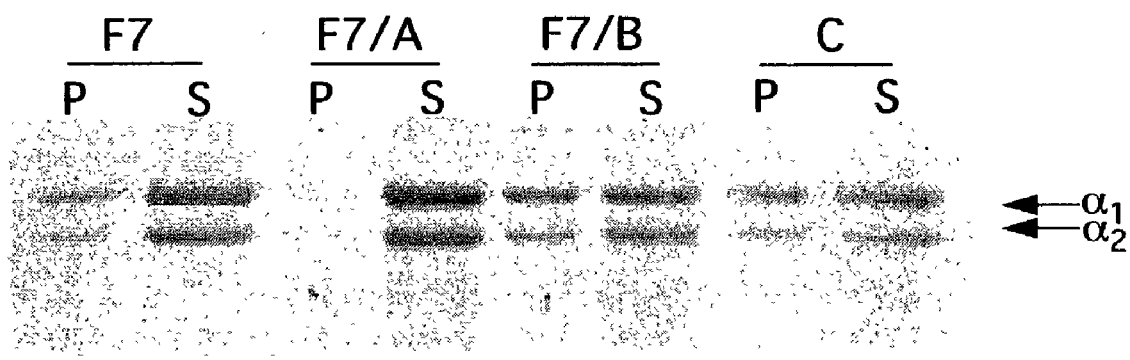

To define the site in the triple helix of type I collagen to which the telopeptides bound, α1(I) and α2(I) chains of type I collagen were isolated and cyanogen bromide peptides were prepared. A filter binding assay was then carried out with a version of the peptides in which the N-terminus was substituted with biotin. As indicated in FIG. 5, the biotinylated derivatives bound to the α1(I) chain but not the α2(I)

chain. As also indicated in FIG. 7, the biotinylated telopeptides bound to CB7 of the α1 chain that contains amino acid residues 552 to 819. There was no apparent binding to any of the other cyanogen bromide fragments.

Figure 8:
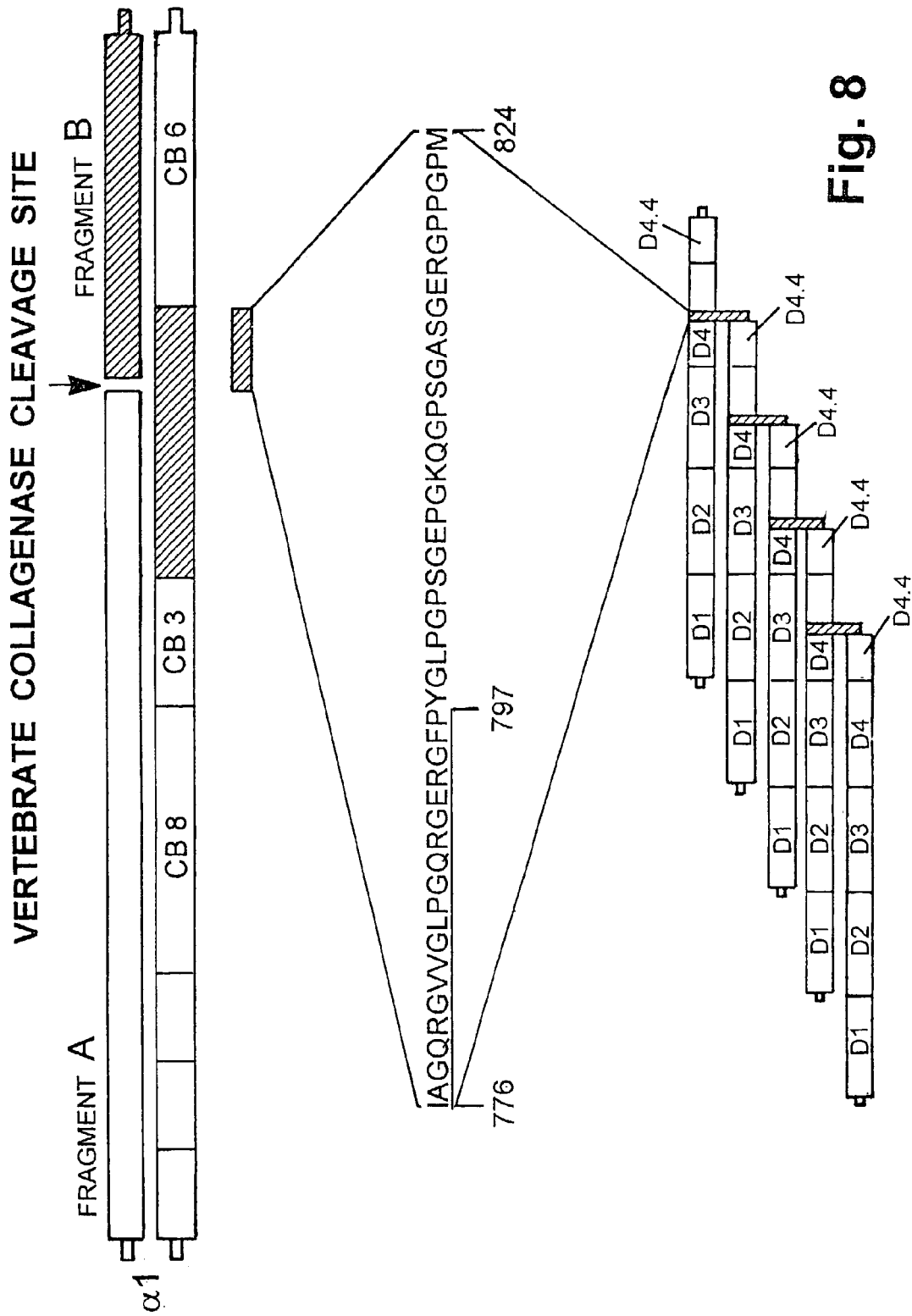
FIG. 8 is a schematic of the binding site in the triple helical domain of the α1(I) chain, wherein a group of residues 776–795 of the sequence corresponds to SEQ ID NO 24 and a group of residues 776–797 of the sequence corresponds to SEQ ID NO 25.
Figure 9A:
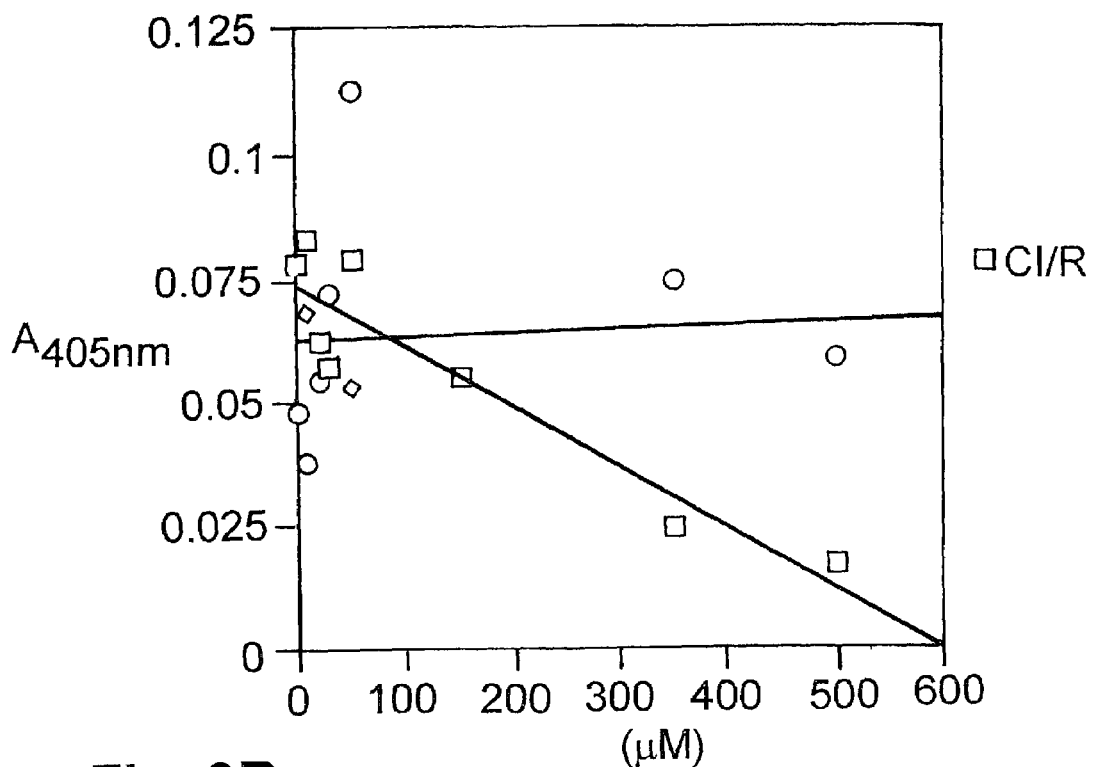
FIGS. 9A and 9B, is a pair of graphs which depict competition by the peptide α1-776/797 for the binding of the C-telopeptides to type I collagen.
Figure 9B:
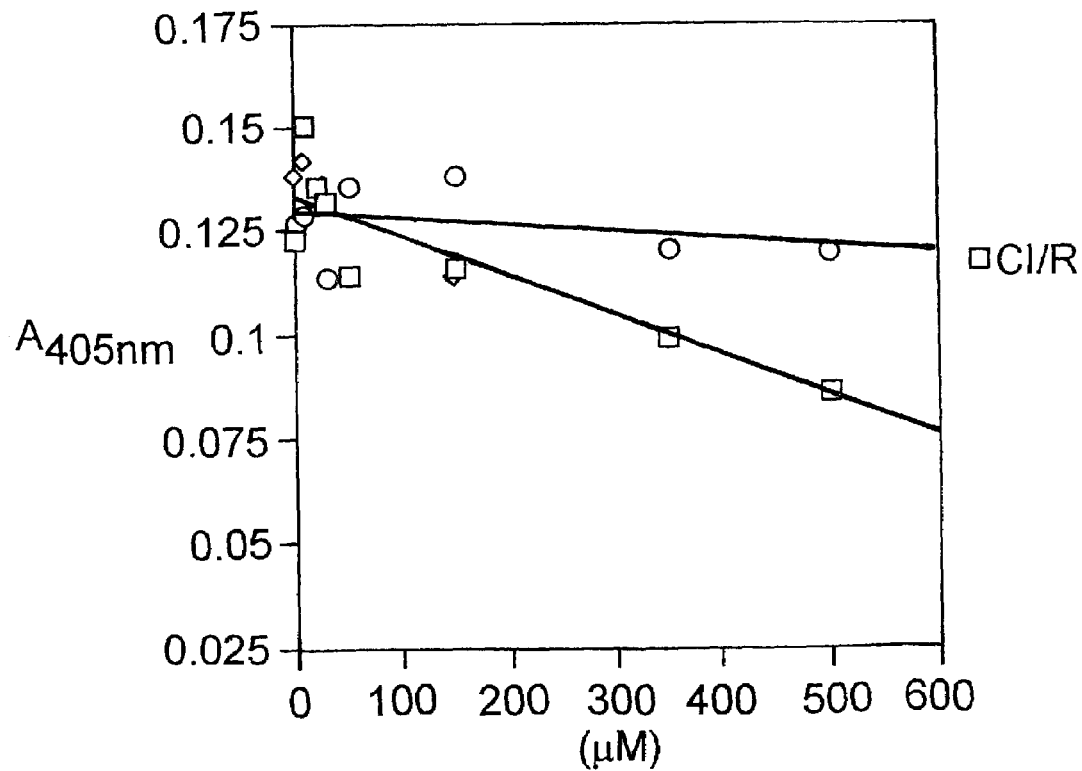

To define further the binding site in the triple helix, vertebrate collagenase A and B fragments of type I collagen were prepared and hybridized with the biotinylated telopeptides. As indicated in FIGS. 8 and 9, the peptides bound specifically to the B fragment of the α1(I) chain. Since vertebrate collagenase cleaves the two a chains of type I collagen between residues 775 and 776, the binding of the peptides to both CB7 and the B fragments of the α1(I) chain indicated that the binding site is between amino acid 776 and 819 of the α1(I) chain.

Defining the Critical Residues in the Peptide F3 and the Triple Helix

Further experiments were primarily concentrated on the F3 peptide with sequence of the C-telopeptide, because it was relatively short and was somewhat repetitive in sequence. Therefore, it lent itself better than the other inhibitory peptides to defining the minimum sequences required and to modeling of the binding interactions.

To define the critical sequences within the peptide F3, several derivatives were prepared. Two peptides that were 9 mers overlapping the central region of the sequence (F7 and F8) were equally effective as the intact F3 (FIGS. 1 and 8 and Table I). Smaller effects on inhibition of fibril assembly were seen with two other fragments (F9 and F 10) (FIGS. 1 and 8 and Table I). Of special interest was that mutating the two aspartate residues in a 9 mer peptide (F7) to serine residues (F7/A) had no effect on inhibition of fibril assembly. However, mutating two tyrosine residues and one phenylalanine residue in the same sequence to serine residues (F7/B) abolished inhibitory effects (FIGS. 1 and 8 and Table I).

To map the binding site in the triple helix still further, a peptide was prepared with the sequence of the amino acids in positions 776 to 797 of the α1(1). The sequence 776 to 797 was selected primarily because it was the most hydrophobic sequence in the region between 776 and 822 that was defined by the experiments with the CNBr peptides and the collagenase fragments (FIG. 9). The peptide α1-776/797 was then used in a competition binding assay in which collagen was bound to the wells of a micro-titer plate, and the plates were incubated with a fixed concentration of one of the biotinylated telopeptides and varying concentrations the peptide α1-776/797. The binding-of the biotinylated peptide was then assayed by incubation with streptavidin-alkaline phosphatase. As indicated-in FIG. 9, the peptide α1-776/797 effectively competed with binding the C-telopeptides of the α1(I) chain (peptide F2) and the α2(I) chain (peptide F3). There was no competition for the binding site between biotinylated telopeptides and F1. Similar results were obtained with the binding of the two N-telopeptides.

Molecular Modeling of the Two Binding Sites

Figures 10A, 10B:
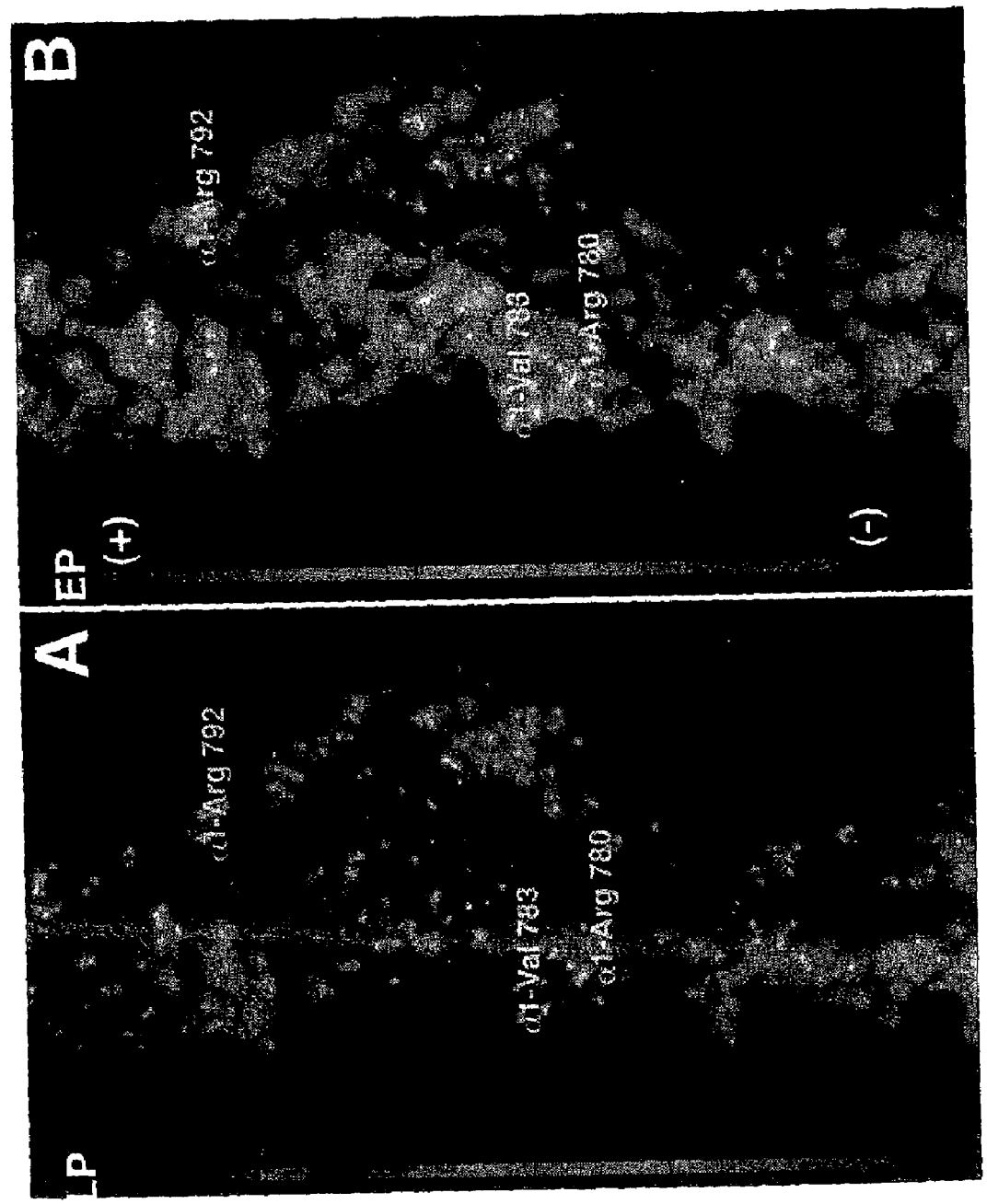
FIGS. 10A and 10B, is a pair of images generated by a computer model of the binding interaction between a 9 amino acid peptide sequence from the C-telopeptide of the α2(I) chain and the triple helix of type I collagen in the region of amino acid α1-766 to 801.

To model the binding of one of the telopeptides to the triple helix, the SYBYL program was first used to model the conformation of one of the 9-amino acid fragments (F7) of the α2(I) C-telopeptide that inhibited fibril assembly (FIGS. 1 and 8 and Table I). Because the aromatic tyrosine and phenylalanine residues tended to form a hydrophobic stack on one side of the polypeptide chain, a single conformation was favored (FIGS. 10A and 10B).

Binding of F7 to the region between residues 781 to 794 of α1(I) was analyzed. The possible binding conformation was interactively identified using the DOCK command. The refined model demonstrated a favorable interaction of hydrophobic groups (FIG. 10A) and electrostatic groups (FIG. 10B).

The results of the experiments described herein resolve a critical question about the self-assembly of type I collagen into fibrils. If the assembly does not depend on specific interactions of binding sites in the monomers as recently suggested by Parkinson et al. (1994, Physical Rev. E. 50:2963–2966), all the peptides tested here should either have had no effect on fibril assembly or inhibited the process to about the same degree. Instead, the results demonstrated that several peptides specifically inhibited the process. Consistent with previous observations, peptides with sequences found in the telopeptides were the most effective. The telopeptide that was most extensively studied, the C-telopeptide of the α2(I) chain, completely prevented fibril assembly if added at or before the first one-third of the lag phase but had much less effect thereafter. Therefore, the binding of the α2(I) C-telopeptide, probably in concert with α1(I) C-telopeptide, is critical for early steps in the assembly process such as formation of a structural nucleus that is essential for further growth of the fibrils. The binding of the C-telopeptides to the region that encompasses residues 776 to 797 places the monomers in quarter D-period stagger (FIG. 9). Therefore, the binding could initiate assembly of a Smith-type pentameter microfibril (Piez, 1984, In: *Extracellular Matrix Biochemistry*, Piez et al., Eds., Elsevier, New York, pp. 1–40; Silver et al., 1992, Proc. Natl. Acad. Sci. 89:9860–9864). In contrast, the binding of the N-telopeptides to about the same region of the α1(I) chain (defined here as residues 776 to 824) places the D-periods out of register by one-third or more of a D-period of 234 residues. Therefore, the binding of the N-telopeptides cannot generate the OD, 1D, 2D, 3D and 4D staggers that are found among many nearest neighbors in fibrils assembled in vivo. Also, the binding of the N-telopeptides does not accurately align the monomers for formation of the major covalent cross-link that forms between the Lys residue at position 9 of the N-telopeptide and the Lys residue at 908 of the α1(I) chain (Piez, 1984, In: *Extracellular Matrix Biochemistry*, Piez et al., Eds., Elsevier, New York, pp. 1–40; Nagan et al., 1994, J. Biol. Chem. 269:22366–22371). Accordingly, there are several possible explanations for the observed binding of the N-telopeptides. One is that the binding occurs only with linear N-telopeptides such as those used here but not with N-telopeptides in the unusual hairpin conformation that is present in the native molecule (Holmes et al., 1993, J. Biol. Chem. 268:15758–15765; Mould et al., 1982, J. Molec. Biol. 195:543–553; Helseth et al., 1979, Biopolymers 18:3005–3014; Helseth et al., 1981, J. Biol. Chem. 256:7118–7128; Vitagliano et al., 1995, J. Mol. Biol. 247:69–80) and that is essential both for assembly into well-ordered fibrils and correct cross-linking (Nagan et al., 1994, J. Biol. Chem. 269:22366–22371). A second explanation is that binding of the N-telopeptides generates aberrant structural nuclei that cannot grow into fibrils and that resemble the "overshoot" structures seen in the assembly of tobacco mosaic virus (Potschka et al., 1988, Biochemistry 27:8481–8491). Preliminary assays with an optical biosensor indicated that the dissociation constant for the binding of the α1-C-telopeptide is about $5 \times 10^{-6}$ M for the dissociation constants and the dissociation constants of the two N-telopeptides are about an order of magnitude greater. Therefore, aberrant structures assembled by binding through the N-telopeptides may have a short half life and may rapidly dissociate into monomers that initiate fibril assembly through binding of C-telopeptides. A third possibility is that binding through the N-telopeptides did not play an important role in fibril assembly until a core of a microfibril is formed and it is only important for lateral growth of the fibril. The last suggestion is consistent with one of the proposed helical models for growth of microfibrils from paraboloidal tips (Silver et al., 1992, Proc. Natl. Acad. Sci. 89:9860–9864). The model required one specific binding step governed by one rate constant (k1) for assembly of monomers in a 1D-stagger to form a Smith-type microfibrillar core and to regulate longitudinal growth of the fibril. It required a second binding step governed by a smaller rate constant (k2) to initiate growth of a new layer of helical sheets of monomers on the microfibrillar core and thereby to regulate lateral growth of the core.

The results presented herein demonstrate that the binding of the C-telopeptide of the α2(I) chain to residues 776 to 797 of the α1(I) chain is directed primarily by hydrophobic interactions, since mutating two tyrosine residues in a 9-amino acid fragment abolished all effects on fibril formation, whereas mutating two aspartate residues had no effect. The modeling experiments indicated that there were conformations of the peptide and the triple helix that allowed good hydrophobic and electrostatic interactions between the 9 amino acid fragment C-telopeptide and the region between 776 and 797. The region contains the C-terminal half of the vertebrate collagenase cleavage site that previously has been designated as a relatively flexible region of the collagen triple-helix (Brown et al., 1977, Biochem. Biophys. Res. Commun. 74:1102–1108). Also, Bhatnagar et al. (1997, J. Biomolec. Struct. Dynamics 14:547–560) recently examined a synthetic peptide with amino acid residues 776 to 780 from the region and found that it had a high potential to form a stable b-bend with the central GIAG sequence that begins in residues 775. Moreover, they demonstrated (Bhatnagar et al., 1997, J. Biomolec. Struct. Dynamics 14:547–560) that the peptide inhibited the binding of fibroblasts to collagen at a concentration of $7.2 \times 10^{-6}$ M. Therefore, the sequence of amino acids in the region may take part in a large number of different binding interactions.

Finally, it is apparent that given the specificity of the binding interactions, the sites defined here provide interesting targets for peptides, peptidomimetics or related compounds that may inhibit the assembly of collagen fibers in pathologic fibrotic conditions. The ability to model binding sites in the triple helix and the conformation of short fragments of the telopeptides provide a rational route for developing inhibitors. The competitive assays on microtiter plates provide a means of high throughput screening for large libraries of potential inhibitors.

EXAMPLE 2

Use of a Phage Display Library to Identify Peptides which Inhibit Collagen Assembly A comrnmercially-available phage-display peptide library was used to identify peptides that bind to the telopeptide binding region of type I collagen (i.e. amino acid residues 776–797). The library comprised phage particles having about $1.9 \times 10^9$ distinct linear peptide sequences.

For the experiments described in this Example, either type I collagen or a 22-mer synthetic peptide having the amino acid sequence of residues 776–797 of type I collagen was bound to the walls of individual wells of microtiter plates. Aliquots of the phage-display peptide library were added to and incubated with the wells. Thereafter, the microtiter wells were rinsed to remove non-specifically-binding library particles, and specifically-binding library particles were eluted using a solution comprising at least one of:

the 22-mer synthetic peptide having the amino acid sequence of residues 776–797 of type I collagen;
type I collagen; and
glycine HCl buffer having a pH of 2.2.

Eluted specifically-binding library particles were added to and incubated with microtiter plates having either type I collagen or the 22-mer synthetic peptide bound to the wells thereof, and washing and elution steps were repeated. A total of three cycles of incubation-washing-elution were performed. Following these three cycles, specifically-binding phage particles were isolated, and the amino acid sequence of the peptide encoded by each of these particles was determined by amplifying and sequencing the nucleic acid contained within the particle.

Amino acid sequences of the random peptide region carried by discrete specifically-binding phage particles are indicated in Table II, together with the identity of the ligand bound to the microtiter wells in each of the three incubation-washing-elution cycles. These isolated peptides, or peptides having no more than about fifty, preferably no more than twenty, even more preferably no more than ten, and still more preferably no more than five amino acid residues at one or both ends thereof, may be used to inhibit collagen self-assembly by contacting a collagen molecule such as a collagen triple helix, with one of these peptides.

TABLE II

| Ligand: 1st Cycle 2nd Cycle 3rd Cycle | Eluent | Amino Acid Sequence(s) of Random Peptide Region(s) | SEQ ID NO: | # of Isolated Particles Having this Sequence | Sequence Similarity Detected |
|---|---|---|---|---|---|
| Type I Collagen Type I Collagen Type I Collagen | pH 2.2 buffer | LIQPPRYSTTVS | 13 | 10 | Versican Core Protein |
| Type I Collagen α1-776/796 | pH 2.2 buffer | LIQPPRYSTTVS SHPWNAQRELSV | 13 14 | 5→ 1 | Versican Core Protein |
| Type I Collagen | | TMATMFTRDLSN | 15 | 1→ | Human TSP-1[A] |
| Type I Collagen Type I Collagen Type I Collagen | Type I Collagen | LLPHSVSIPPDA | 16 | 10 | Versican Core Protein |
| Type I Collagen Type I Collagen Type I Collagen | α1-776/796 | SHALPLTWSTAA | 17 | 10 | |
| α1-776/796 Type I Collagen | pH 2.2 buffer | TFWHLTPPRGYY NHVHRMHATPAY | 18 19 | 2→ 4 | LysH, TSP-2 |

TABLE II-continued

| Ligand: 1st Cycle 2nd Cycle 3rd Cycle | Eluent | Amino Acid Sequence(s) of Random Peptide Region(s) | SEQ ID NO: | # of Isolated Particles Having this Sequence | Sequence Similarity Detected |
|---|---|---|---|---|---|
| α1-776/796 | | VHWWIPVSTGTA | 20 | 2→ | Chordin |
| | | HSSLKLPNLSHR | 21 | 1 | |
| α1-776/796 | pH 2.2 buffer | VHWWIPVSTGTA | 20 | 6→ | Chordin |
| α1-776/796 | | TFWHLTPPRGYY | 18 | 3→ | LysH[B], TSP-2 |
| α1-776/796 | | | | | |
| α1-776/796 | Type I Collagen | YGSPHPSRPPGA | 22 | 10 | Versican Core Protein |
| α1-776/796 | | | | | |
| α1-776/796 | | | | | |
| α1-776/796 | α1-776/796 | QLLEPVNLSTGP | 23 | 7 | |
| α1-776/796 | | SHALPLTWSTAA | 17 | 1 | |
| α1-776/796 | | YGSPHPSRPPGA | 22 | 1→ | Versican Core Protein |

Note:
[A]TSP means thrombospondin
[B]LysH means lysine hydroxylase

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of identifying a type I collagen assembly-inhibiting peptide, said method comprising immobilizing a collagen species on a support, wherein said collagen species is selected from the group consisting of human type I collagen and a human type I collagen peptide;

contacting said support with a labeled peptide in the presence or absence of an unlabeled test peptide, wherein said labeled peptide is know to inhibit collagen self-assembly; and assessing the amount of labeled peptide bound to said support, wherein a lower amount of labeled peptide bound to said support in the presence of said test peptide compared with the level of binding of said labeled peptide to said support in the absence of said test peptide is an indication that said test peptide is a type I collagen assembly-inhibiting peptide.

2. A method of identifying a type I collagen assembly-inhibiting peptide, said method comprising immobilizing collagen species on a support, wherein said collagen species is selected from the group consisting of human type I collagen and a human type I collagen peptide;

contacting said support with at least one peptide-bearing particle which comprises a test peptide; and assessing whether said peptide-bearing particle binds with said support, whereby binding of said peptide-bearing particle to said support is an indication that said test peptide is a type I collagen assembly-inhibiting peptide.

3. The method of claim 2, wherein said human type I collagen peptide has the amino acid sequence SEQ ID NO: 25 of amino acid residues 776 through 797, inclusive, of the α1 chain of human type I collagen.

4. The method of claim 2, wherein said human type I collagen peptide has the amino acid sequence SEQ ID NO: 24 of amino acid residues 776 through 795, inclusive, of the α1 chain of human type I collagen.

5. The method of claim 2, wherein said peptide-bearing particle is a phage.

6. The method of claim 5, wherein said at least one phage comprises a phage display peptide library.

7. The method of claim 2, wherein said support is rinsed prior to assessing whether said peptide-bearing particle binds with said support.

8. The method of claim 7, wherein said assessing comprises contacting said support with a collagen un-binding eluent and detecting the presence of said peptide-bearing particle in said eluent.

9. The method of claim 8, wherein said collagen un-binding eluent is selected from the group consisting of Tris-glycine buffer at a pH of about 2.2, a suspension comprising human type I collagen, and a suspension comprising a peptide having the amino acid sequence SEQ ID NO: 24 of amino acid residues 776 through 795, inclusive, of the α1 chain of human type I collagen.

10. The method of claim 8, wherein said peptide-beaming particle is a phage, and wherein said detecting the presence of said phage comprises detecting the ability of said phage to lyse cultured cells.

11. The method of claim 8, wherein said peptide-bearing particle in said eluent is contacted with a second support, wherein said second support has the same or a different collagen species immobilized thereon.

* * * * *

```
                         SEQUENCE LISTING

<160> NUMBER OF SEQ ID NOS: 23

<210> SEQ ID NO 1
<211> LENGTH: 16
<212> TYPE: PRT
<213> ORGANISM: Homo sapiens

<400> SEQUENCE: 1

Ala Lys Gly Ala Ala Gly Leu Pro Gly Val Ala Gly Ala Pro Gly Leu
1               5                   10                  15

<210> SEQ ID NO 2
<211> LENGTH: 24
<212> TYPE: PRT
<213> ORGANISM: Homo sapiens

<400> SEQUENCE: 2

Gly Ala Pro Gly Ile Leu Gly Leu Pro Gly Ser Arg Gly Glu Arg Gly
1               5                   10                  15

Leu Pro Gly Val Ala Gly Ala Val
            20

<210> SEQ ID NO 3
<211> LENGTH: 25
<212> TYPE: PRT
<213> ORGANISM: Homo sapiens

<400> SEQUENCE: 3

Ala Asp Gly Pro Ala Gly Ala Pro Gly Thr Pro Gly Pro Gln Gly Ile
1               5                   10                  15

Ala Gly Gln Arg Gly Val Val Gly Leu
            20                  25

<210> SEQ ID NO 4
<211> LENGTH: 17
```

```
<212> TYPE: PRT
<213> ORGANISM: Homo sapiens

<400> SEQUENCE: 4

Gln Leu Ser Tyr Gly Tyr Asp Glu Lys Ser Thr Gly Gly Ile Ser Val
1               5                   10                  15
Pro

<210> SEQ ID NO 5
<211> LENGTH: 26
<212> TYPE: PRT
<213> ORGANISM: Homo sapiens

<400> SEQUENCE: 5

Ser Ala Gly Phe Asp Phe Ser Phe Leu Pro Gln Pro Pro Gln Glu Lys
1               5                   10                  15
Ala His Asp Gly Gly Arg Tyr Tyr Arg Ala
            20                  25

<210> SEQ ID NO 6
<211> LENGTH: 15
<212> TYPE: PRT
<213> ORGANISM: Homo sapiens

<400> SEQUENCE: 6

Gly Gly Gly Tyr Asp Phe Gly Tyr Asp Gly Asp Phe Tyr Arg Ala
1               5                   10                  15

<210> SEQ ID NO 7
<211> LENGTH: 9
<212> TYPE: PRT
<213> ORGANISM: Homo sapiens

<400> SEQUENCE: 7

Gly Gly Gly Tyr Asp Phe Gly Tyr Asp
1               5

<210> SEQ ID NO 8
<211> LENGTH: 9
<212> TYPE: PRT
<213> ORGANISM: Homo sapiens

<400> SEQUENCE: 8

Gly Tyr Asp Gly Asp Phe Tyr Arg Ala
1               5

<210> SEQ ID NO 9
<211> LENGTH: 10
<212> TYPE: PRT
<213> ORGANISM: Homo sapiens

<400> SEQUENCE: 9

Gly Tyr Asp Phe Gly Tyr Asp Gly Asp Phe
1               5                   10

<210> SEQ ID NO 10
<211> LENGTH: 6
<212> TYPE: PRT
<213> ORGANISM: Homo sapiens

<400> SEQUENCE: 10

Asp Phe Arg Tyr Arg Ala
1               5
```

-continued

<210> SEQ ID NO 11
<211> LENGTH: 9
<212> TYPE: PRT
<213> ORGANISM: Homo sapiens

<400> SEQUENCE: 11

Gly Gly Gly Tyr Ser Phe Gly Tyr Ser
1               5

<210> SEQ ID NO 12
<211> LENGTH: 9
<212> TYPE: PRT
<213> ORGANISM: Homo sapiens

<400> SEQUENCE: 12

Gly Gly Gly Ser Asp Ser Gly Ser Asp
1               5

<210> SEQ ID NO 13
<211> LENGTH: 12
<212> TYPE: PRT
<213> ORGANISM: Artificial Sequence
<220> FEATURE:
<223> OTHER INFORMATION: Phage Display Library Peptide

<400> SEQUENCE: 13

Leu Ile Gln Pro Pro Arg Tyr Ser Thr Thr Val Ser
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Phage Display Library Peptide

<400> SEQUENCE: 14

Ser His Pro Trp Asn Ala Gln Arg Glu Leu Ser Val
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Phage Display Library Peptide

<400> SEQUENCE: 15

Thr Met Ala Thr Met Phe Thr Arg Asp Leu Ser Asn
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Phage Display Library Peptide

<400> SEQUENCE: 16

Leu Leu Pro His Ser Val Ser Ile Pro Pro Asp Ala
1               5                   10

<210> SEQ ID NO 17
<211> LENGTH: 12
<212> TYPE: PRT
<213> ORGANISM: Artificial Sequence

```
<220> FEATURE:
<223> OTHER INFORMATION: Phage Display Library Peptide

<400> SEQUENCE: 17

Ser His Ala Leu Pro Leu Thr Trp Ser Thr Ala Ala
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Phage Display Library Peptide

<400> SEQUENCE: 18

Thr Phe Trp His Leu Thr Pro Pro Arg Gly Tyr Tyr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Phage Display Library Peptide

<400> SEQUENCE: 19

Asn His Val His Arg Met His Ala Thr Pro Ala Tyr
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Phage Display Library Peptide

<400> SEQUENCE: 20

Val His Trp Trp Ile Pro Val Ser Thr Gly Thr Ala
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Phage Display Library Peptide

<400> SEQUENCE: 21

His Ser Ser Leu Lys Leu Pro Asn Leu Ser His Arg
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Phage Display Library Peptide

<400> SEQUENCE: 22

Tyr Gly Ser Pro His Pro Ser Arg Pro Pro Gly Ala
1               5                   10

<210> SEQ ID NO 23
<211> LENGTH: 12
<212> TYPE: PRT
<213> ORGANISM: Artificial Sequence
<220> FEATURE:
```

-continued

```
<223> OTHER INFORMATION: Phage Display Library Peptide

<400> SEQUENCE: 23

Gln Leu Leu Glu Pro Val Asn Leu Ser Thr Gly Pro
1               5                   10
```